(12) United States Patent
Zouaghi

(10) Patent No.: US 12,702,563 B2
(45) Date of Patent: Aug. 11, 2026

(54) TIBIAL TRIAL INSERT SYSTEM

(71) Applicant: Aesculap AG, Tuttlingen (DE)

(72) Inventor: Housseyn Zouaghi, Metz (FR)

(73) Assignee: Aesculap AG, Tuttlingen (DE)

( * ) Notice: Subject to any disclaimer, the term of this patent is extended or adjusted under 35 U.S.C. 154(b) by 406 days.

(21) Appl. No.: 18/576,445

(22) PCT Filed: Jul. 4, 2022

(86) PCT No.: PCT/EP2022/068385
§ 371 (c)(1),
(2) Date: Jan. 4, 2024

(87) PCT Pub. No.: WO2023/280749
PCT Pub. Date: Jan. 12, 2023

(65) Prior Publication Data

US 2025/0090336 A1 Mar. 20, 2025

(30) Foreign Application Priority Data

Jul. 5, 2021 (EP) .................................... 21183675

(51) Int. Cl.
*A61F 2/38* (2006.01)

(52) U.S. Cl.
CPC .......... *A61F 2/389* (2013.01); *A61F 2220/00* (2013.01)

(58) Field of Classification Search
CPC ........... A61B 17/025; A61B 2017/0268; A61F 2/4657; A61F 2/4684
See application file for complete search history.

(56) References Cited

U.S. PATENT DOCUMENTS 5,733,292 A * 3/1998 Gustilo ................ A61B 17/025 606/88
2012/0158152 A1 6/2012 Claypool et al.
(Continued)

FOREIGN PATENT DOCUMENTS

JP 6521671 B2 5/2019
WO 2019115744 A1 6/2019

OTHER PUBLICATIONS

Search Report received in PCT Application No. PCT/EP2022/068385 dated Sep. 20, 2022, 7 pages.
(Continued)

*Primary Examiner* — Andrew Yang
(74) *Attorney, Agent, or Firm* — Christopher A. Rothe; CM Law

(57) ABSTRACT

A tibial trial insert system includes a bearing component having a superior articulating surface for articulation with a distal femoral surface, a plate component having an inferior fixation surface for fixation to a proximal tibia, and an adjustment arrangement for adjusting a proximal/distal spacing between the bearing component and the plate component. The adjustment arrangement includes an adjustment device having a superior connector element that engages an inferior surface of the bearing component, an inferior base element adapted to be placed upon a superior surface of the plate component, and a telescopic mechanism coupled to the connector element and the base element. The telescopic mechanism can adjust a thickness of the adjustment device. At least one shim is insertable between the superior surface of the plate component and an inferior surface of the base element for adjusting a height level of the adjustment device relative to the plate component.

12 Claims, 8 Drawing Sheets

(56) References Cited

U.S. PATENT DOCUMENTS

| | | | |
|---|---|---|---|
| 2012/0232660 | A1 | 9/2012 | Davenport |
| 2013/0138112 | A1 | 5/2013 | Young |
| 2014/0277543 | A1 | 9/2014 | Fox et al. |
| 2015/0359642 | A1 | 12/2015 | Claypool et al. |
| 2016/0278944 | A1 | 9/2016 | D'lima et al. |

OTHER PUBLICATIONS

Written Opinion received in PCT Application No. PCT/EP2022/068385 dated Sep. 20, 2022, 7 pages.

* cited by examiner

TIBIAL TRIAL INSERT SYSTEM

CROSS-REFERENCE TO RELATED APPLICATIONS

This application is the United States national stage entry of International Application No. PCT/EP2022/068385, filed on Jul. 4, 2022, and claims priority to European Application No. 21183675.4, filed on Jul. 5, 2021. The contents of International Application No. PCT/EP2022/068385 and European Application No. 21183675.4 are incorporated by reference herein in their entireties.

FIELD

The invention relates to a tibial trial insert system.

BACKGROUND

During a total knee arthroplasty, tibial trial insert systems are typically used to assist a surgeon in determining a size, shape or other configuration of a permanent prosthesis that is designed to replace a portion of the knee joint. In particular, such tibial trial insert systems are used to determine a relative spacing between a femoral component and a tibial component of the permanent prosthesis.

US 2015/0359642 A1 discloses a tibial trial insert system comprising a bearing component, a plate component and an adjustment arrangement. The bearing component has a superior articulating surface for articulation with a distal femoral surface. The plate component has an inferior fixation surface for fixation to a proximal tibia. The adjustment arrangement is configured for adjusting a proximal/distal spacing between the bearing component and the plate component. The adjustment arrangement comprises a plurality of shims, each shim configured to be slidable between the bearing component and the plate component to change the relative proximal/distal spacing.

WO 2019/115744 A1 discloses a tibial trial insert system comprising a first plate coupled to a second plate by means of an adjustment arrangement. The adjustment arrangement includes a plurality of adjustors. The adjustors are actuatable to adjust the proximal/distal spacing between the first plate and the second plate. The plurality of adjustors consists of three adjustors arranged in a triangular configuration, wherein each adjustor comprises a scissor lift mechanism. Each of the three scissor lift mechanisms is separately actuatable by means of separate actuator bolts.

SUMMARY

It is an object of the present invention to provide a tibial trial insert system that allows a simple, versatile and stable adjustment of the relative spacing between the bearing component and the plate component.

According to the invention, a tibial trial insert system is provided, said tibial trial insert system comprising: a bearing component having a superior articulating surface for articulation with a distal femoral surface; a plate component having an inferior fixation surface for fixation to a proximal tibia; and an adjustment arrangement for adjusting a proximal/distal spacing between the bearing component and the plate component, wherein the adjustment arrangement comprises: an adjustment device having a superior connector element configured to engage with an inferior surface of the bearing component, an inferior base element adapted to be placed at least indirectly upon a superior surface of the plate component, and having a telescopic mechanism operatively coupled to the connector element and to the base element, wherein the telescopic mechanism is user-operable for adjusting a thickness of the adjustment device; and at least one shim configured for insertion between the superior surface of the plate component and an inferior surface of the base element for adjusting a height level of the adjustment device in relation to the plate component. The invention allows a particularly simple, versatile and stable adjustment of the proximal/distal spacing. The adjustment is done by means of the adjustment device and additionally by means of the at least one shim. For this purpose, the proximal/distal thickness of the adjustment device is variable by means of the telescopic mechanism. The telescopic mechanism is actuatable by a user for changing the proximal/distal spacing between the connector element and the base element—and thus the thickness of the adjustment device. Additionally, the proximal/distal height level of the adjustment device can be varied relative to the plate component. For this purpose, the at least one shim is provided. The at least one shim can be slidably inserted between the adjustment device and the plate component. Insertion of the at least one shim raises the adjustment device in proximal direction, i.e. in the direction of the bearing component, relative to the plate component and increases the height level accordingly. To reduce the height level, the at least one shim can be removed from between the inferior surface of the base element and the superior surface of the plate component. This lowers the adjustment device in distal direction relative to the plate component. The thickness of the adjustment device and its height level are independently adjustable, which allows for a versatile adjustment of the proximal/distal spacing between the bearing component and the plate component. “Thickness of the adjustment device” refers to the overall height of the adjustment device in proximal/distal direction. “Height level” refers to the distance between the inferior surface of the base element and the superior surface of the plate component in proximal/distal direction. Preferably, the connector element is configured to removably engage with the inferior surface of the bearing component. The base element can be placed directly upon the superior surface of the plate component in case the at least one shim is not inserted between the superior surface of the plate component and the inferior surface of the base element. Alternatively, in case the at least one shim is inserted, the base element is placed upon the at least one shim and thus indirectly upon the superior surface of the plate component. To change the thickness of the adjustment device, the telescopic mechanism is retractable and extendable in proximal/distal direction. Preferably, the telescopic mechanism comprises at least one scissor lift mechanism, linkage, translation screw or the like. In this document the terms “superior”, “inferior”, “anterior”, “posterior”, “medial”, “lateral”, “proximal” and “distal” are used according to their standard anatomical definitions. In this document the phrase “proximal/distal spacing” denotes a spacing that extends in a proximal and/or distal direction. Analogously, the phrase “anterior/posterior” means anterior and/or posterior; the phrase “medial/lateral” means medial and/or lateral. The plate component can also be termed “tibial plateau component”.

In one embodiment, the base element comprises an inferior fastening portion, and the at least one shim comprises a complementary superior fastening portion, wherein the inferior fastening portion and the superior fastening portion are configured to slidably engage in anterior/posterior direction and to form-fittingly engage in proximal/distal direction and in medial/lateral direction. By means of the inferior fastening portion of the base element and the superior fastening portion of the at least one shim, the at least one shim and the base element—and thus the adjustment device—can be detachably fastened to each other. This causes a mechanical stabilization of the tibial trial insert system. The inferior fastening portion and the superior fastening portion are designed and/or shaped to be complementary to each other. In one embodiment the superior fastening portion comprises at least one recess and the inferior fastening portion comprises at least one complementary protrusion or vice versa. When the at least shim is slidably inserted between the base element and the plate component, the superior fastening portion slidably engages with the inferior fastening portion in anterior/posterior direction. Once the at least one shim is completely inserted, the superior fastening portion and the inferior fastening portion engage form-fittingly in proximal/distal direction and in medial/lateral direction.

In one embodiment, the plate component comprises a receiving recess open in proximal direction and configured for receiving the base element, and the plate component comprises an insertion aperture open in anterior/posterior direction and leading into the receiving recess, wherein the insertion aperture allows sliding the at least one shim into the receiving recess in anterior/posterior direction. This provides additional mechanical stabilization. At the same time, the insertion of the at least one shim and thus the adjustment of the proximal/distal spacing is further simplified. The receiving recess is countersunk into the plate component in distal direction. Once received within the receiving recess, the base element is restrained in distal direction. Preferably, the base element is also restrained in anterior/posterior direction and in medial/lateral direction. The insertion aperture facilitates the insertion of the at least one shim. It allows to slide the at least one shim into the receiving recess and underneath the adjustment device when the base element is already received within the receiving recess. After insertion, the at least one shim is restrained between the plate component and the base element in proximal/distal direction and within the receiving recess in medial/lateral direction. The at least one shim can be inserted in posterior direction and removed in the opposite anterior direction or vice versa.

In one embodiment, the adjustment arrangement comprises at least one further shim configured for insertion between the superior surface of the plate component and the inferior surface of the base element and/or an inferior surface of the shim. The at least one further shim allows for a further adjustment of the height level of the adjustment device. The at least one further shim can be inserted instead of and/or in addition to the at least one shim. In one embodiment, the shim and the further shim have identical dimensions, in particular with respect to their proximal/distal thickness. In other embodiments, the shim and the further shim differ with respect to their design, shape and/or at least with respect to one dimension, in particular their proximal/distal thickness. In a preferred embodiment, the shim comprises an inferior fastening portion and the further shim comprises a complementary superior fastening portion, wherein the inferior fastening portion of the shim and the superior fastening portion of the further shim are configured to slidably engage in anterior/posterior direction and to form-fittingly engage in proximal/distal direction and in medial/lateral direction. Moreover, in case the base element comprises an inferior fastening portion, the superior fastening portion of the further shim is preferably configured to slidably engage in anterior/posterior direction and to form-fittingly engage in proximal/distal direction and in medial/lateral direction with the inferior fastening portion of the base element.

In one embodiment, the telescopic mechanism comprises at least a first translation screw and a second translation screw, each translation screw having a screw member in thread engagement with a nut member, wherein a user-operated movement of the first translation screw and the second translation screw causes an adjustment of the thickness of the adjustment device. The translation screws translate a user-operated, i.e. manual, turning motion of the respective nut member into a linear motion of the respective screw member. The linear motion is oriented in proximal/distal direction. In a preferred embodiment, both screw members are fixedly attached to an inferior surface of the connector element. Alternatively, the screw members are integral with the connector element. Each screw member comprises an external and/or male thread. In a preferred embodiment, the nut members are rotatably mounted on the base element. Preferably, each nut member comprises an internal and/or female thread. Preferably, the first translation screw and the second translation screw are spaced apart in medial/lateral direction. In one embodiment, the first translation screw and the second translation screw are adapted for a separate manual actuation and thus movement. Alternatively, the telescopic mechanism can be adapted for a synchronized manual actuation and thus movement of both translation screws. The screw member and the nut member of the first translation screw can also be denoted as first screw member and first nut member, respectively. The screw member and the nut member of the second translation screw can also be denoted as second screw member and second nut member, respectively.

In one embodiment, the nut member of the first translation screw and the nut member of the second translation screw each comprise external teeth, the external teeth of the nut members being at least indirectly interlocked for synchronized movement of the first translation screw and the second translation screw. The synchronized movement of both translation screws allows for an improved and further simplified adjustment of the proximal/distal spacing. Moreover, the present inventors have recognized that a separate movement of the translation screws may cause an unintended deformation of the bearing component and thus the articulating surface. The synchronized movement of both translation screws is achieved by means of the interlocking external teeth of the nut members. Due to the external teeth, the nut members each form kind of a gear wheel. In one embodiment, the external teeth of the first nut member and the external teeth of the second nut member interlock with each other directly. In a preferred embodiment, the external teeth are interlocked indirectly by means of at least one gear wheel with external teeth, the external teeth of the at least one gear wheel being interlocked with both the external teeth of the first nut member and the external teeth of the second nut member.

In one embodiment, the telescopic mechanism comprises a control gear wheel interlocked with the external teeth of both nut members such that a rotation of the control gear wheel causes synchronized rotations of the nut members. Preferably, the control gear wheel is rotatably mounted on the base element. In one embodiment, the control gear wheel is adapted for direct manual rotation, i.e. a direct user-operated actuation. In a further embodiment, the control gear wheel is adapted for an indirect user-operated actuation, for example by means of interacting with a further gear wheel, a tool or the like.

In one embodiment, the control gear wheel forms a nut member of a third translation screw of the telescopic mechanism. The third translation screw comprises the nut member and a screw member in thread engagement with said nut member. The nut member and the screw member of the third translation screw can also be denoted as third nut member and third screw member, respectively. In this embodiment, the control gear wheel has multiple functions. One function is to synchronize the rotations of the first nut member and the second nut member and thus the adjustment movement of the first translation screw and the second translation screw. A further function is to serve as the nut member of the third translation screw. The design and function of the third translation screw are essentially identical to the design and function of the first and second translation screws. To avoid repetition, what has already been said with respect to the first and second translation screws also applies to the third translation screw mutatis mutandis.

In one embodiment, the tibial trial insert system comprises a handle detachably attached to the adjustment device, the handle having a manipulation mechanism operatively coupled to the telescopic mechanism and configured such that a user-operated manipulation of the manipulation mechanism causes movement of the telescopic mechanism to thereby adjust the thickness of the adjustment device. The handle allows ergonomic and safe handling of the adjustment device. To this end, the handle can be attached to the adjustment device. After handling the adjustment device by means of the handle, the handle can be detached from the adjustment device. A plug-in, latching and/or snap-in connection can be formed between the handle and the adjustment device, said connection being formed between at least one connection element provided on the handle and a complementary connection element provided on the adjustment device. When the handle is attached to the adjustment device, the manipulation mechanism is operatively coupled to the telescopic mechanism. When the handle is detached from the adjustment device, the manipulation mechanism is decoupled from the telescopic mechanism. Preferably, the manipulation mechanism comprises a manipulation element movably mounted on the handle, wherein the manipulation element is adapted for a rotational and/or translational movement by the user, and wherein rotational and/or translational motion of the manipulation element causes a movement of the manipulation mechanism and thereby a movement of the telescopic mechanism.

In one embodiment, the handle is elongated between a proximal end and a distal end, wherein the handle comprises at least one snap-fit element disposed at the distal end and configured for establishing a snap-fit connection with a complementary snap-fit element of the adjustment device. This embodiment allows a simple and robust attachment and detachment of the handle. Preferably, the at least one snap-fit element is integral with the handle, in particular its distal end. Preferably, the complementary snap-fit element is integral with the adjustment device, in particular with its base element. For establishing the snap-fit connection, the snap-fit element and/or the complementary snap-fit element is deformed elastically. In a preferred embodiment, the snap-fit element is a male element and the complementary snap-fit element is a female element. Preferably, the snap-fit element and the complementary snap-fit element interact in anterior/posterior direction, i.e. the handle and the adjustment device are moved relative to each other in anterior/posterior direction for attachment and detachment.

In one embodiment the manipulation mechanism comprises a manipulation gear wheel configured to be rotated manually, the manipulation gear wheel being at least indirectly interlocked with a gear wheel, in particular the control gear wheel, of the telescopic mechanism. This allows for a surprisingly simple and robust design. The manipulation gear wheel is rotatably mounted on the handle. Preferably, the manipulation mechanism, in particular the manipulation gear wheel, is arranged at the distal end of the handle. The manipulation gear wheel is preferably adapted to be rotated by means of a thumb of the user. In this case, the manipulation gear wheel can also be denoted as thumb wheel. The manipulation gear wheel comprises external teeth that interlock with external teeth of the gear wheel of the telescopic mechanism. The gear wheels are interlocked as long as the handle is attached to the adjustment device. Once the handle is detached from the adjustment device, the manipulation gear wheel and the gear wheel are not interlocked.

In one embodiment, the manipulation mechanism comprises at least one transmission gear wheel interlocked with the manipulation gear wheel and the gear wheel of the telescopic mechanism. The transmission gear wheel transmits the user-induced motion of the manipulation gear wheel onto the gear wheel of the telescopic mechanism. The transmission gear wheel allows an ergonomic arrangement of the manipulation gear wheel. Moreover, changing the specifications of the transmission gear wheel allows for a simple change of a transmission ratio between the movement of the manipulation gear wheel and the telescopic mechanism.

BRIEF DESCRIPTION OF THE DRAWINGS

In the following, an embodiment of the invention will be described in detail with reference to the drawings. Throughout the drawings, the same elements will be denoted by the same reference numerals. The drawings schematically show.

DETAILED DESCRIPTION

Figure 1:
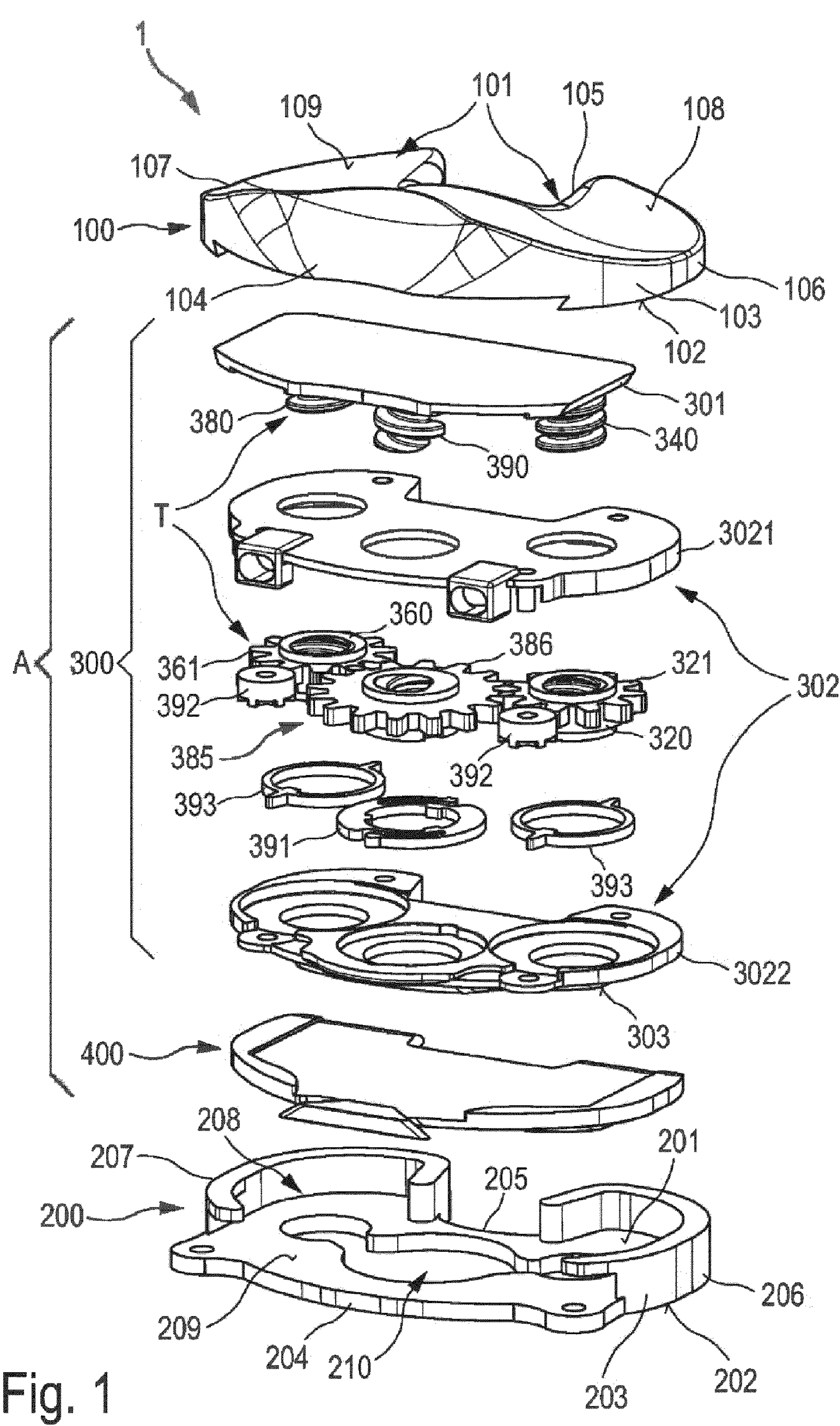
FIG. 1 shows in a perspective exploded view an embodiment of a tibial trial insert system according to the invention having a bearing component, a plate component and an adjustment arrangement, the adjustment arrangement comprising an adjustment device and at least one shim.

According to FIGS. 1 to 4, 14 and 15, a tibial trial insert system 1 is provided for use in a knee joint replacement surgery. The tibial trial insert system 1 comprises a bearing component 100, a plate component 200 and an adjustment arrangement A, the adjustment arrangement A comprising an adjustment device 300 and at least one shim 400. In the embodiment as illustrated, the tibial trial insert system 1 further comprises a handle 500.

The bearing component 100 has a superior articulating surface 101, an opposing inferior surface 102 and a peripheral wall 103 extending from the inferior surface 102 to the superior articulating surface 101. The bearing component 100 further includes an anterior side 104, a posterior side 105, a lateral side 106 and a medial side 107. The superior articulating surface 101 is configured for articulation with a natural or prosthetic condyle of a distal femur. The superior articulating surface 101 includes a lateral articulating surface portion 108 and a medial articulating surface portion 109.

The plate component 200 has a superior surface 201, an opposing inferior fixation surface 202 and a peripheral wall 203. The plate component 200 further includes an anterior side 204, a posterior side 205, a lateral side 206 and a medial side 207. The inferior fixation surface 202 is configured for direct or indirect fixation to a proximal end of a tibia.

The adjustment arrangement A allows an adjustment of a proximal/distal spacing between the bearing component 100 and the plate component 200. In other words, the function of the adjustment arrangement A is to adjust and/or vary the proximal/distal position of the superior articulating surface 101 relative to the plate component 200, in particular relative to the inferior fixation surface 202. Such a spacing or height adjustment is required for trial reposition in knee joint replacement surgery. Said trial reposition is a preceding operation step of the actual knee joint replacement, wherein sizes, dimensions and/or shapes of the tibial and femoral implant components required for a functional replacement of the knee joint are determined. This application related background of the tibial trial insert system 1 is well-known to a person skilled in the art. Therefore, no further explanations are needed in that respect.

Both the adjustment device 300 and the at least one shim 400 of the adjustment arrangement A serve to adjust the proximal/distal spacing between the bearing component 100 and the plate component 200.

The adjustment device 300 comprises a superior connector element 301, an inferior base element 302 and a telescopic mechanism T.

Figure 6:
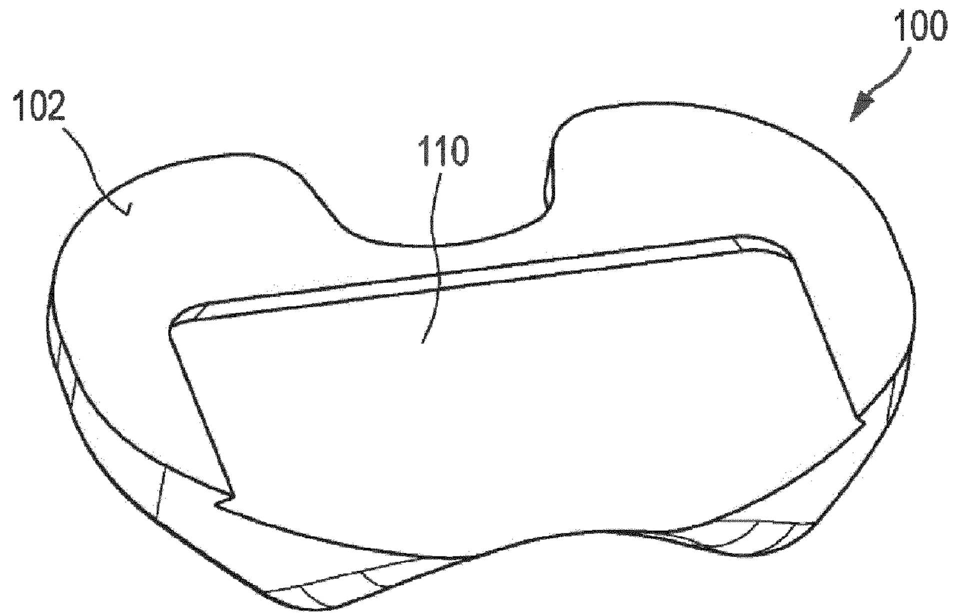
FIG. 6 shows a further perspective detail view of the bearing component without the connector element.
Figure 7:
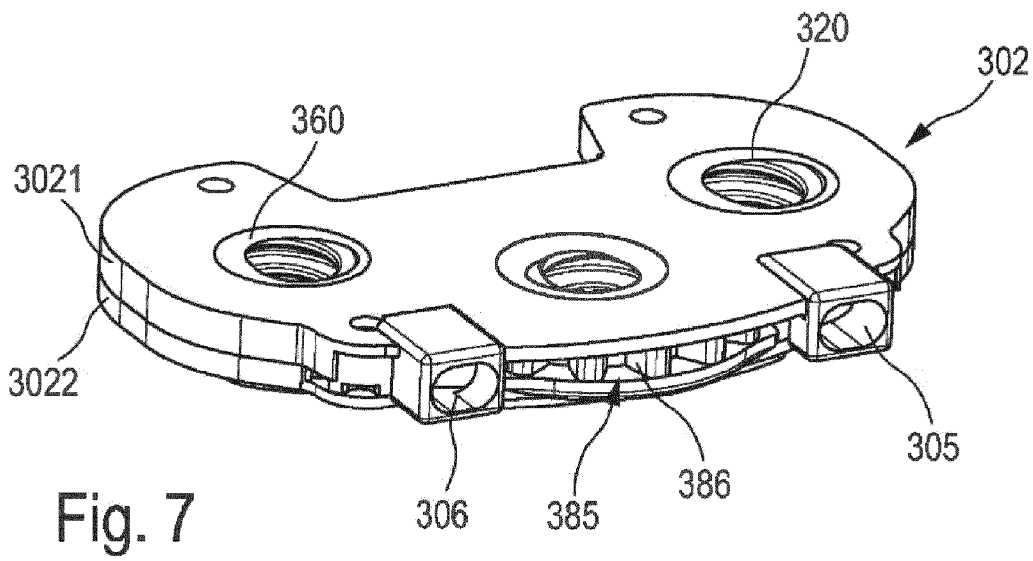
FIG. 7 shows a perspective detail view of the adjustment device omitting the connector element.
Figure 8:
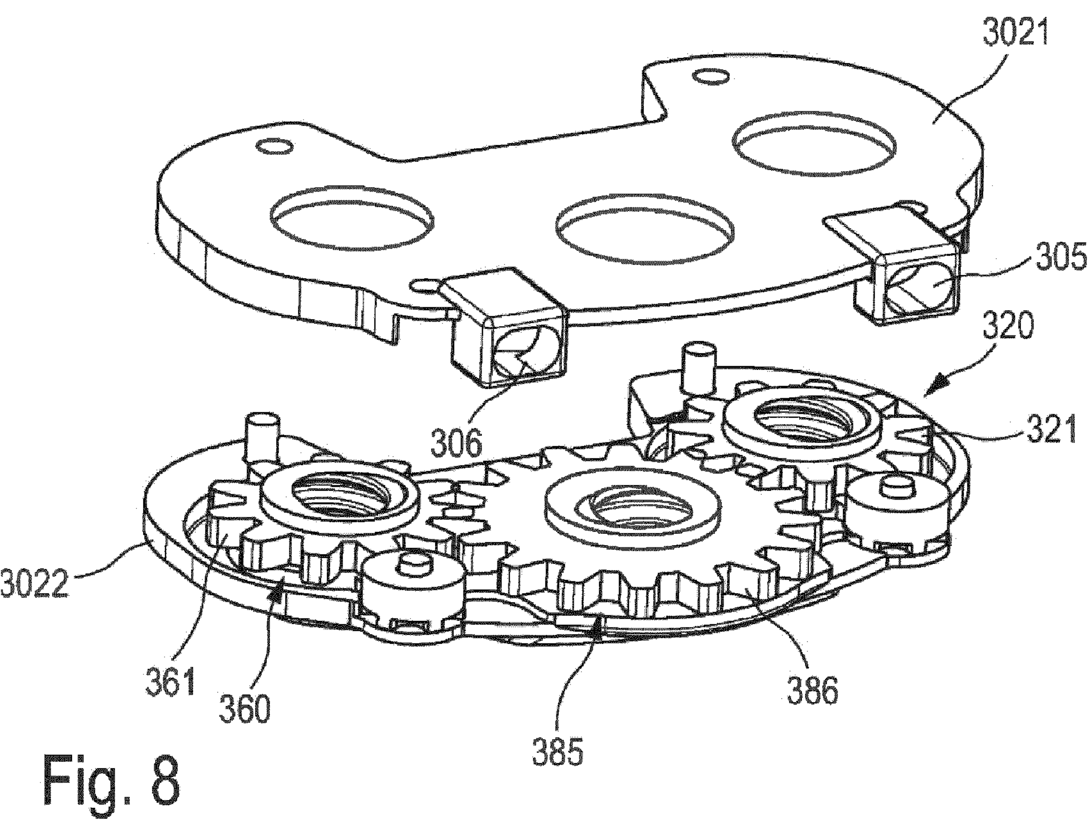
FIG. 8 shows a further perspective and partially exploded view of the adjustment device according to FIG. 7.

The superior connector element 301 is configured to removably engage with the inferior surface 102 of the bearing component 100. The bearing component 100 comprises an engagement portion 110 (see FIG. 6). The engagement portion 110 is countersunk into the inferior surface 102 in proximal direction. The engagement portion 110 and the connector element 301 are configured to slidably engage in anterior/posterior direction and to form-fittingly engage in proximal/distal direction and in medial/lateral direction. To this end, the engagement portion 110 is designed in the form of a dovetail guide open in anterior direction. In a further embodiment, the connector element is fixedly attached and/or integral with the inferior surface of the bearing component.

The inferior base element 302 is adapted to be placed at least indirectly upon the plate component 200 in distal direction. In configurations of the tibial trial insert system 1 that make use of the at least one shim 400 (see FIG. 1, 4, 14, 15), the base element 302 is placed directly upon the at least one shim (and/or a further shim) and thus indirectly on the plate component 200. In configurations of the tibial trial insert system 1 that do not make use of the at least one shim 400 (and further shims) (see FIG. 2, 3), the base element 200 is directly placed upon the plate component 200. In the embodiment as illustrated, the base element 302 has a two-part design comprising an upper first base element part 3021 and a lower second base element part 3022. In a further embodiment, the base element has a single-part design.

The telescopic mechanism T is operatively coupled to the connector element 301 and to the base element 302. The telescopic mechanism T is actuatable by a user for adjusting a proximal/distal thickness of the adjustment device 300. Varying the proximal/distal thickness of the adjustment device 300 by means of the telescopic mechanism T leads to an adjustment of the proximal/distal spacing between the bearing component 100 and the plate component 200. In view of the present invention, the design of the telescopic mechanism T as illustrated in the figures is advantageous, but not necessarily essential. Other embodiments comprise a different design of the telescopic mechanism. Details of the design and function of the telescopic mechanism will therefore be discussed in more detail below.

The at least one shim 400 is configured for insertion between the plate component 200 and the base element 302 for adjusting a proximal/distal height level of the adjustment device 300 relative to the plate component 200. In particular, the at least one shim 400 is configured for insertion between superior surface 201 of the plate component 200 and an inferior surface 303 of the base element 302. In the embodiment as illustrated, the inferior surface 303 is located on the second base element part 3022.

Figure 2:
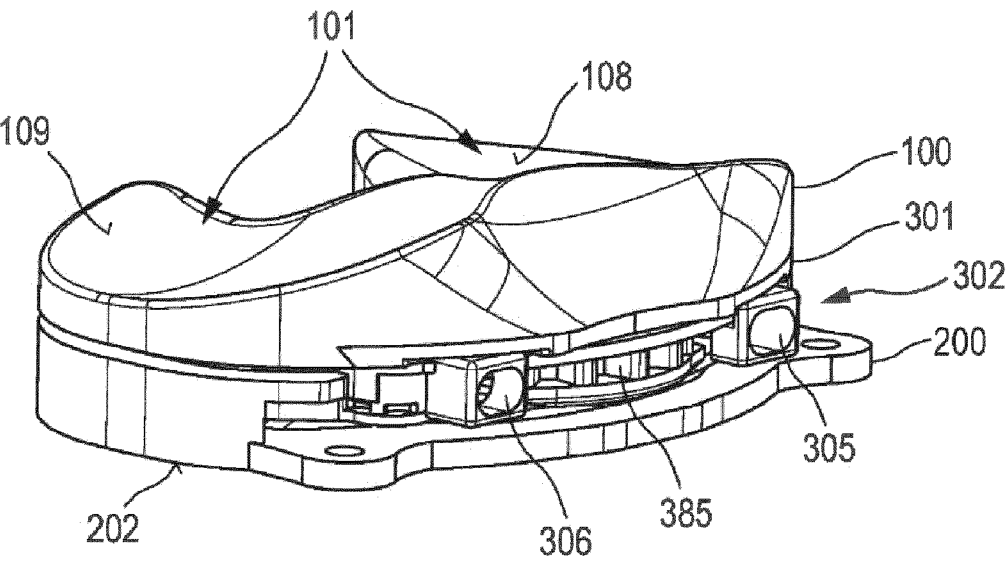
FIGS. 2 and 3 show perspective views of the tibial trial insert system according to FIG. 1 without the at least one shim, wherein the adjustment device is adjusted to have a first thickness (FIG. 2) and a second thickness (FIG. 3)
Figure 3:
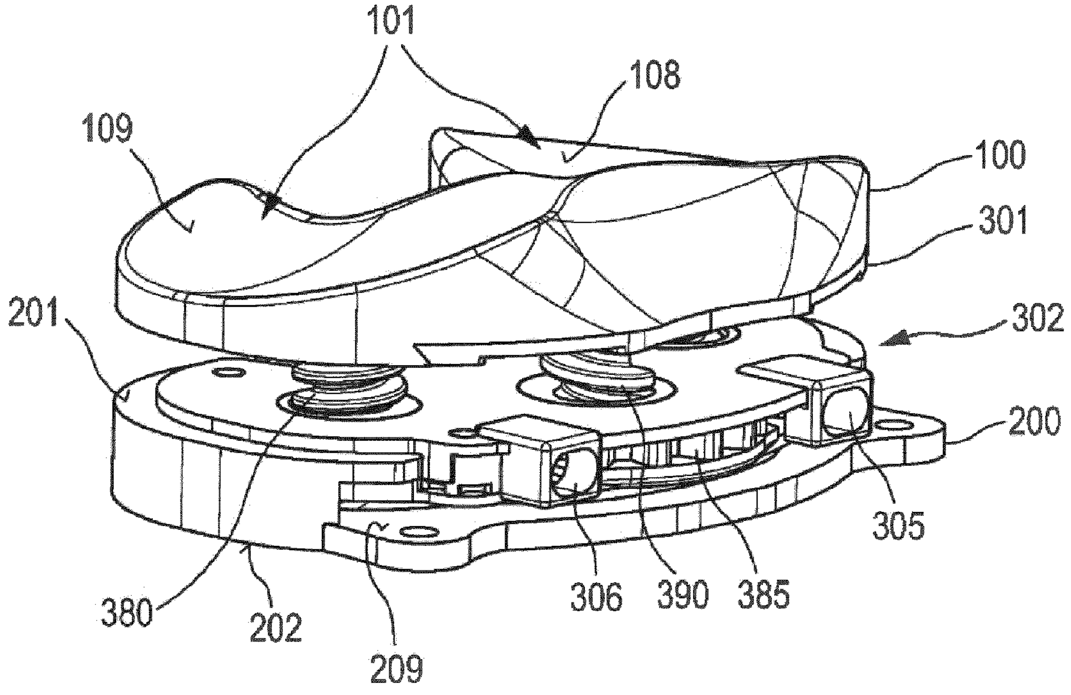
Figure 4:
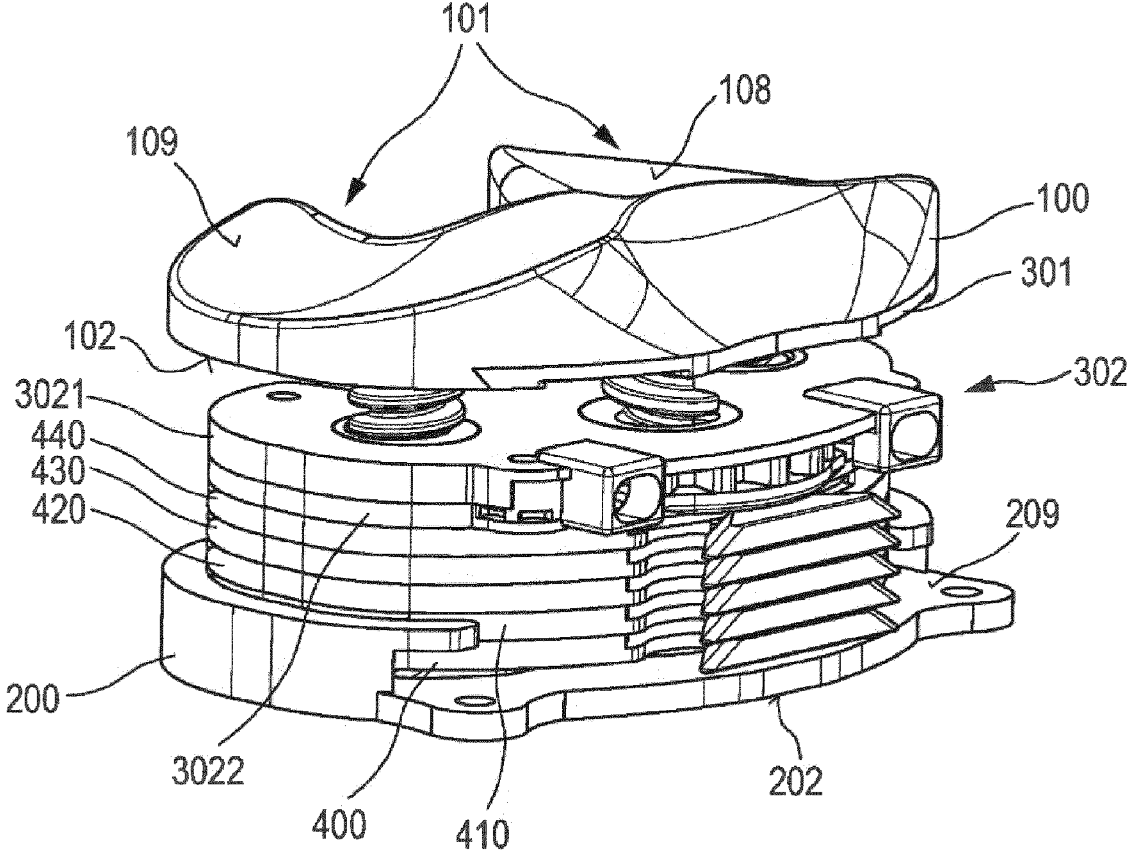
FIG. 4 shows a further perspective view of the tibial trial insert system according to FIGS. 1 to 3, wherein the adjustment device is adjusted to the second thickness, and wherein a height level of the adjustment device relative to the plate component is adjusted by means of several shims inserted between the plate component and the adjustment device.
Figure 5:
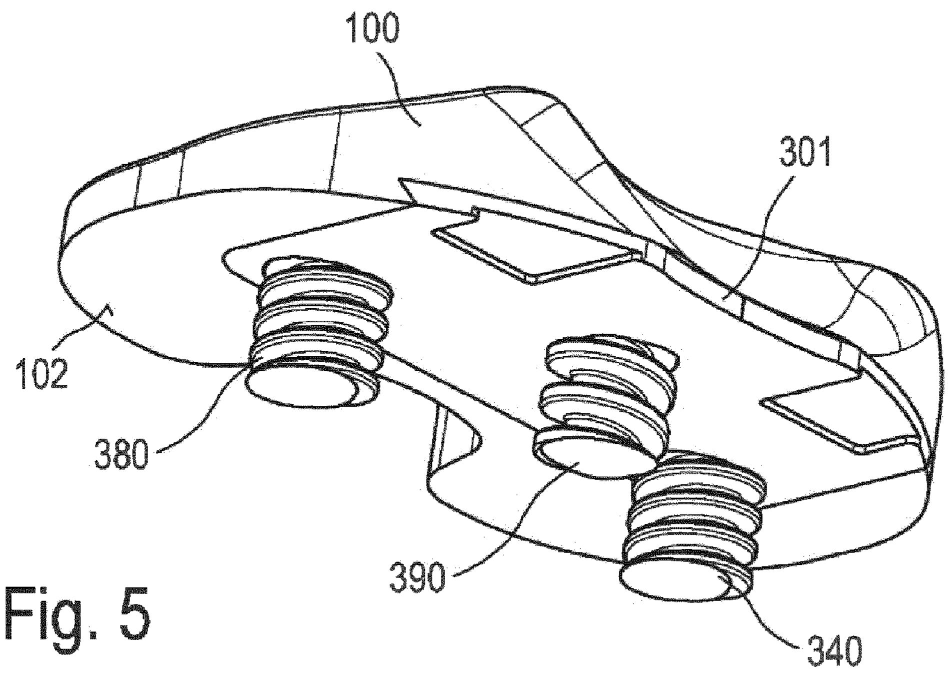
FIG. 5 shows a perspective detail view of the bearing component together with a connector element of the adjustment device.

FIGS. 2, 3 and 4 depict different configurations of the tibial trial insert system 1 having different adjustments of the proximal/distal spacing between the bearing component 100 and the plate component 200. Said different configurations can be denoted as first configuration (FIG. 2), second configuration (FIG. 3) and third configuration (FIG. 4).

In the first configuration and the second configuration, the tibial trial insert system 1 does not make use of the at least one shim 400. Hence, the adjustment device 300 directly engages with the plate component 200. For that purpose, the plate component 200 comprises a receiving recess 208 open in proximal direction and configured for receiving the base element 302. The receiving recess 208 is countersunk into the plate component 200 in distal direction and surrounded by the peripheral wall 203. The receiving recess 208 has a bottom surface 209. In the present embodiment, the bottom surface 209 and the superior surface 201 are congruent. The bottom surface 209 forms a distal boundary of the receiving recess 208. When received within the receiving recess 208, the base element 302, in particular its inferior surface 303, rests upon the bottom surface 209. Moreover, the base element 302 is form-fittingly restrained in anterior/posterior direction and in medial/lateral direction within the receiving recess and/or by means of the peripheral wall 203.

In the first configuration (FIG. 2), the adjustment device 300 is adjusted to a first thickness, the first thickness being the minimum thickness of the adjustment device 300. In the second configuration (FIG. 3) the adjustment device 300 is adjusted to a second thickness, the second thickness being the maximum thickness of the adjustment device 300.

For further increasing the spacing between the bearing component 100 and the plate component 200, the at least one shim 400 can be inserted. In the third configuration (FIG. 4) the at least one shim 400 is inserted to lift the adjustment device 300 in proximal direction in relation to the plate component 200. By lifting the adjustment device 300, its height level is increased, and thus the proximal/distal spacing between the bearing component 100 and the plate component 200 is further adjusted and/or increased.

In the third configuration as depicted in FIG. 4, the at least one shim 400 is inserted together with further shims 410, 420, 430, 440. Said shims 400, 410, 420, 430, 440 can be denoted as first shim 400, second shim 410, third shim 420, fourth shim 430 and fifth shim 440. The shims 400 to 440 are stacked on top of each other. Adding shims lifts the adjustment device, removing shims lowers the adjustment device.

In configurations not making use of the at least one shim 400 (or any one of the further shims 410 to 440) the adjustment device 300 is positioned at its minimum height level, which can be denoted as zero height level.

To facilitate the insertion of the shims 400 to 440, the plate component 200 comprises an insertion aperture 210. The insertion aperture 210 is open in anterior/posterior direction and leads into the receiving recess 208. The insertion aperture 210 allows sliding the shims underneath the base element 302 and into the receiving recess 208. In the embodiment as illustrated, the insertion aperture 210 forms an anterior opening within the peripheral wall 203.

Starting from the zero height level (see FIG. 2, 3), the different height level of the adjustment device 300 can be achieved as follows. A first height level is achieved by sliding the fifth shim 440 through the insertion aperture 210 into the receiving recess 208. By doing so, the fifth shim 440 is positioned between the bottom surface 209 and the inferior surface 303. Additionally inserting the fourth shim 430 lifts the adjustment device 300 to a second height level. In this configuration, the fourth shim 430 is positioned between the bottom surface 209 and an inferior surface of the fifth shim 440. Further height levels of the adjustment device 300 can be adjusted by proceeding with the third, second and first shim 420, 410, 400, wherein the first shim 400 is the last and lower-most shim to be inserted.

On each of said height levels, the telescopic mechanism T is user-operable or for extension in proximal direction and retraction in distal direction for adjusting the thickness of the adjustment device 300.

Figure 9:
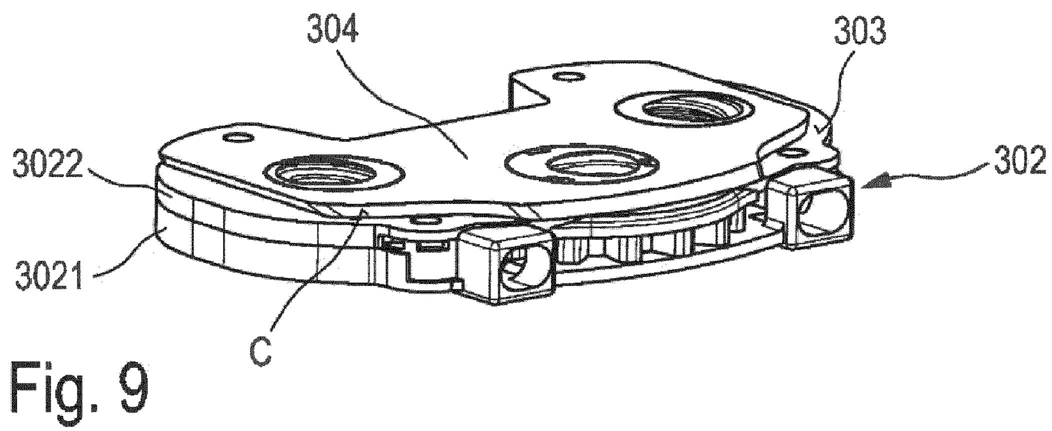
FIG. 9 shows a further perspective view of the adjustment device according to FIGS. 7 and 8 with a line of sight directed towards an inferior side of the adjustment device.
Figure 10:
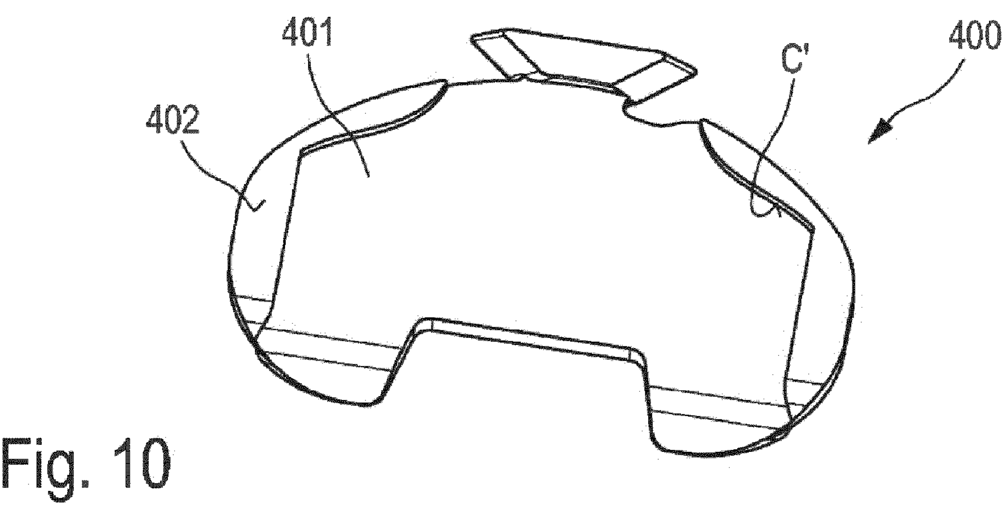
FIG. 10 shows a perspective detail view of the at least one shim with a line of sight directed towards a superior side.
Figure 11:
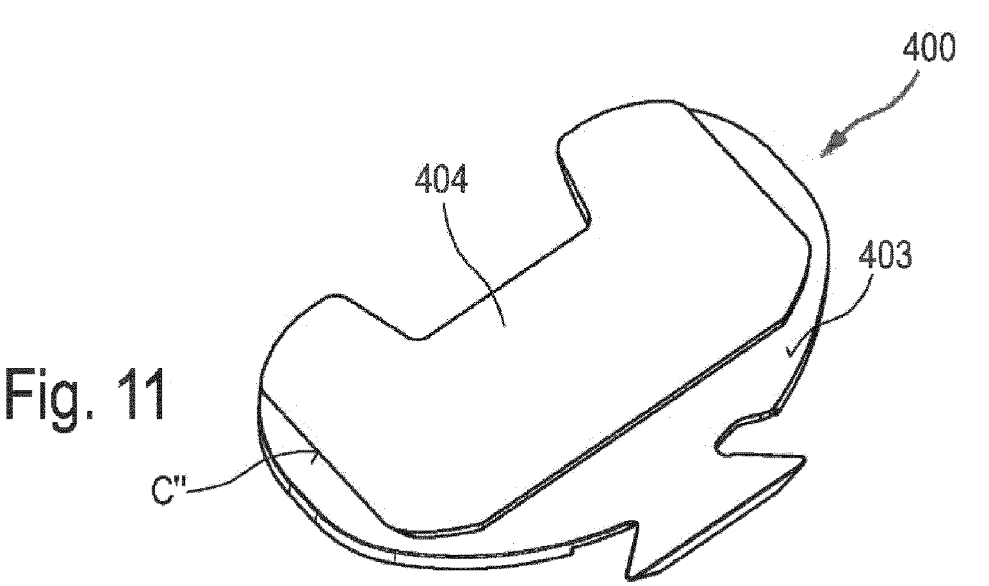
FIG. 11 shows a further perspective detail view of the shim according to FIG. 10 with a line of sight directed towards an inferior side.
Figure 12:
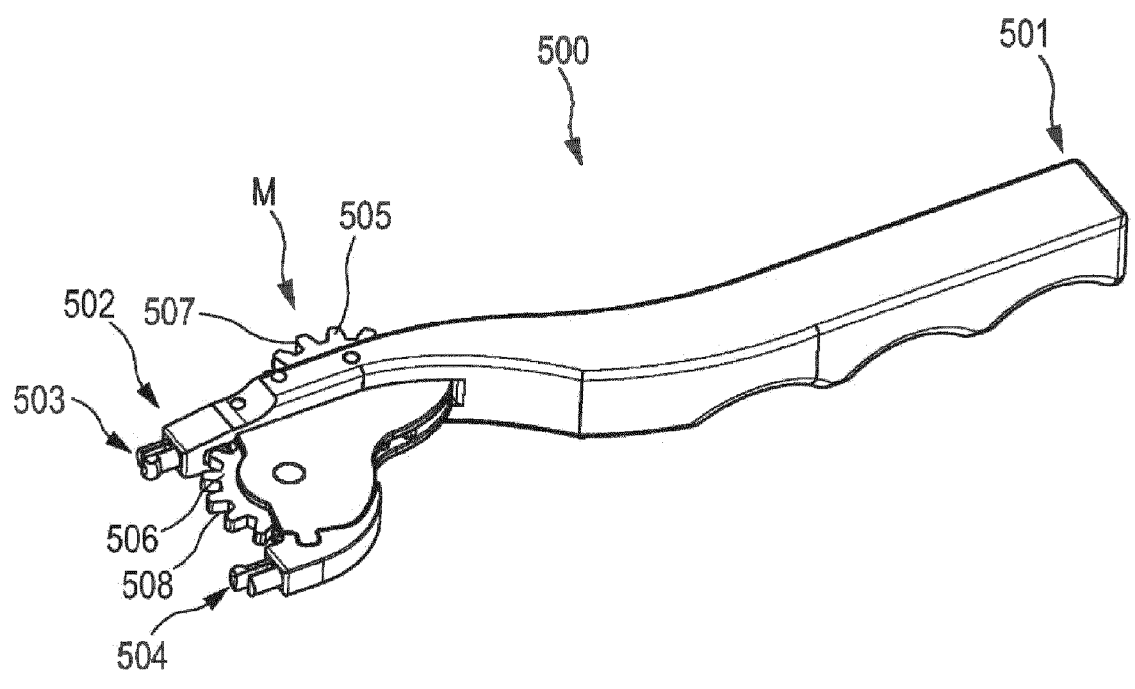
FIG. 12 shows a perspective view of a handle of the tibial trial insert system configured for attachment to and manual adjustment of the adjustment device.

To improve the stability of the tibial trial insert 1 in its third configuration (FIG. 4) or any other configuration that involves at least one shim, the base element 302 comprises an inferior fastening portion 304 (FIG. 9) and each of the shims 400 to 440 comprises a complementary superior fastening portion 401 (FIG. 10). The inferior fastening portion 304 and the complementary superior fastening portion 401 are configured to slidably engage in anterior/posterior direction and to form-fittingly engage in proximal/distal direction and in medial/lateral direction. In the embodiment as illustrated, the inferior fastening portion 304 of the base element 302 is a protrusion that protrudes from the inferior surface 303 in distal direction. The design of the superior fastening portion of the shims 400 to 440 is illustrated with respect to the first shim 400 (FIG. 10), wherein the same holds for the further shims 410 to 440 analogously. The superior fastening portion 401 forms a complementary recess that is countersunk into a superior surface 402 of the first shim 400 in distal direction. The inferior fastening portion 304 has an outer contour C that is complementary to an inner contour C' of the superior fastening portion 401. The medial and lateral sides of the outer contour C and the inner contour C' each comprise an undercut. Said undercuts fixate the base element 302 onto the first shim 400 in proximal direction.

The first shim 400 further comprises an inferior surface 403 opposing the superior surface 402. At its inferior side, the first shim 400 comprises an inferior fastening portion 404. The inferior fastening portion 404 forms a protrusion that protrudes from the inferior surface 403 in distal direction. The inferior fastening portion 404 is configured to slidably and form-fittingly engage with the superior fastening portion of the further shims 410 to 440. The remaining shims 410 to 440 each comprise such an inferior fastening portion, too. The inferior fastening portion 404 comprises an outer contour C" that is at least partially complementary to the inner contour C'.

In the third configuration (FIG. 4), the inferior fastening portion 304 of the base element 302 slidably and form-fittingly engages with the superior fastening portion of the fifth shim 440. The inferior fastening portion of the fifth shim 440 slidably and form-fittingly engages with the superior fastening portion of the fourth shim 430. The inferior fastening portion of the fourth shim 430 slidably and form-fittingly engages with the superior fastening portion of the third shim 420. The inferior fastening portion of the third shim 420 slidably and form-fittingly engages with the superior fastening portion of the second shim 410. The inferior fastening portion of the second shim 410 slidably and form-fittingly engages with the superior fastening portion of the first shim 400. The first shim 400 is restrained within the receiving recess 208 (FIG. 4).

In the embodiment as illustrated, the telescopic mechanism T comprises at least a first translation screw 320, 340 and a second translation screw 360, 380 (see FIG. 1). The first translation screw 320, 340 comprises a first nut member 320 and a first screw member 340 in thread engagement with each other. The second translation screw 360, 380 comprises a second nut member 360 and a second screw member 380 in thread engagement with each other. The thickness of the adjustment device 300 is adjustable by means of a movement of the first translation screw 320, 340 and the second translation screw 360, 380.

Both nut members 320, 360 comprise an internal or female thread. Both screw members 340, 380 comprise an external or male thread.

Both nut members 320, 360 are rotatably mounted on the base element 302 so that they can each rotate around a rotation axis parallel to the proximal/distal direction. In the embodiment as illustrated, the nut members 320, 360 each are mounted between the first base element part 3021 and the second base element part 3022. Both screw members 340, 380 are integral with the connector element 301. In a further embodiment the screw members are formed as separate parts that are fixedly attached to the connector element. Both screw members 340, 380 extend from an inferior surface of the connector element 301 in distal direction. The first screw member 340 extends coaxially to the rotation axis of the first nut member 320. The second screw member 380 extends coaxially to the rotation axis of the second nut member 360.

In one embodiment, the first translation screw and the second translation screw are each adapted for separate actuation and/or movement. In the embodiment as illustrated, however, the movement of the first translation screw 320, 340 and the movement of the second translation screw 360, 380 are synchronized by means of a control gear wheel 385. The control gear wheel 385 comprises external teeth 386 that are interlocked with external teeth 321 of the first nut member 320 and external teeth 361 of the second nut member 360. The control gear wheel 385 is rotatably mounted on the base element 302, in particular between the first base element part 3021 and the second base element part 3022. The control gear wheel 385 rotates about a rotation axis that is parallel to the rotation axis of the first nut member 320 and the second nut member 360, respectively. A rotation of the control gear wheel 385 causes a synchronous rotation of the first nut member 320 and the second nut member 360 and thus a synchronous translations of the first translation screw 320, 340 and the second translation screw 360, 380.

Moreover, in the embodiment as illustrated, the control gear wheel 385 forms a nut member of a third translation screw 385, 390 of the telescopic mechanism T. The third translation screw 385, 390 comprises the control gear wheel 385 as nut member and a screw member 390, which can be denoted as third screw member.

In the embodiment as illustrated, the adjustment device 300 further comprises a latching arrangement with a latching wheel 391. The latching arrangement provides the user with tactile and acoustic feedback that a specific proximal/distal spacing has been reached. The indicator arrangement comprises indicator wheels 392 that are intermittently operatively connected to the nut members 320, 360 by means of driver wheels 393. The indicator arrangement allows a step-by-step display of the reached proximal/distal spacing. However, neither the latching arrangement nor the indicator arrangement is of primary importance with respect to the present invention. Further explanations are therefore omitted.

In one embodiment, the control gear wheel 385 is adapted for direct manual actuation by a user. However, in the embodiment as illustrated, the tibial trial insert system 1 comprises said handle 500 that allows an indirect user-operated actuation of the telescopic mechanism T, in particular its control gear wheel 385.

Figure 13:
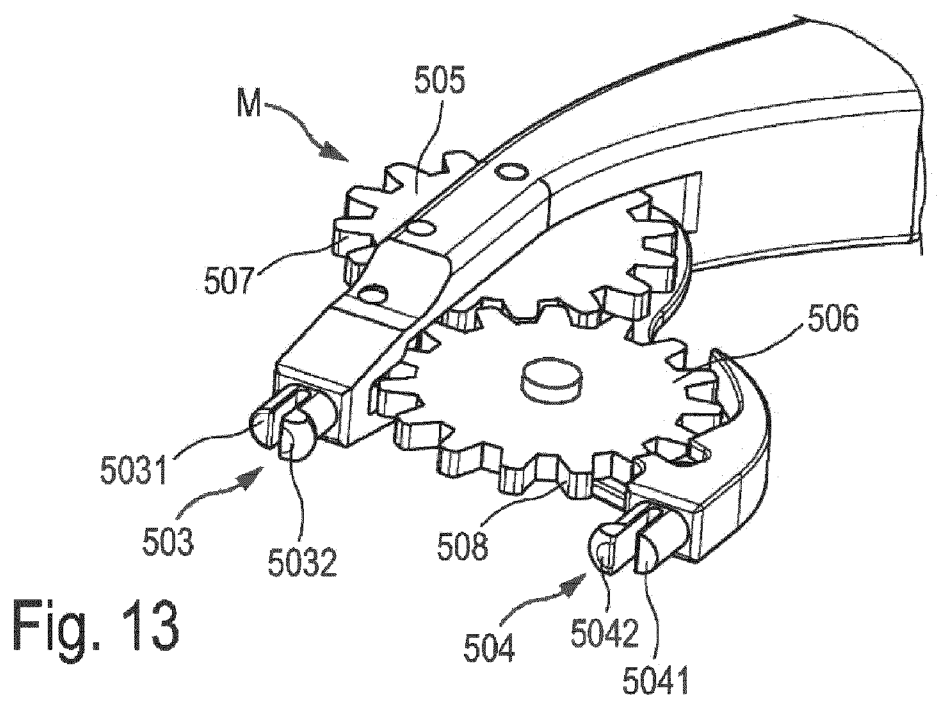
FIG. 13 shows a perspective detail view of a distal end of the handle according to FIG. 12 and FIGS. 14 and 15 show perspective views of different configurations of the tibial trial insert system, wherein the handle is detachably attached to the adjustment device.
Figure 14:
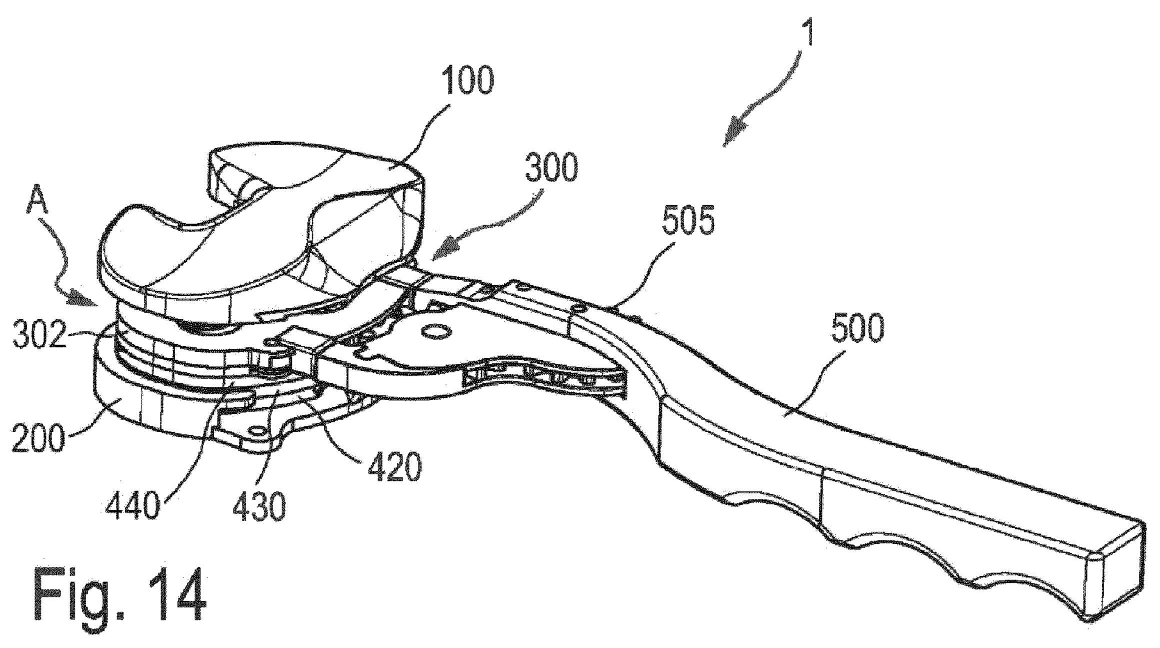
Figure 15:
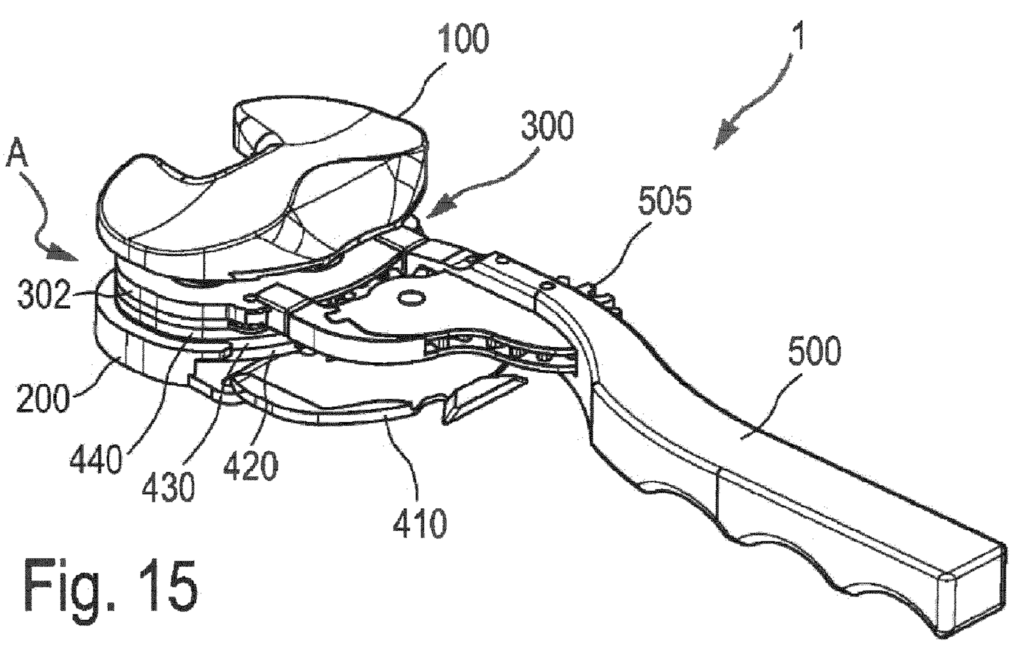

In the configurations shown in FIGS. 14, 15, the handle 500 is detachably attached to the adjustment device 300. In the configurations shown in FIGS. 1, 2, 3, 4, 12, 13, the handle 500 is detached from the adjustment device 300. The handle 500 is elongated between a proximal end 501 and a distal end 502. At its distal end 502 the handle 500 comprises at least one snap-fit element 503. In the embodiment as illustrated, the handle 500 comprises two snap-fit elements, i.e. the first snap-fit element 503 and a second snap-fit element 504. The first snap-fit element 503 is configured for establishing a releasable snap-fit connection with a complementary first snap-fit element 305 of the adjustment device 300. The second snap-fit element 504 is configured for establishing a releasable snap-fit connection with a complementary second snap-fit element 306 of the adjustment device 300. In the embodiment as illustrated, the snap-fit elements 503, 504 of the handle 500 both are male elements. The complementary snap-fit elements 305, 306 of the adjustment device 300 both are designed as female elements and are configured for receiving the snap-fit elements 305, 306 in anterior/posterior direction. The first snap-fit element 503 and the second snap-fit element 504 are spaced apart in medial/lateral direction, wherein the first snap-fit element 503 is located laterally and the second snap-fit element is located medially. The same holds analogously with respect to the location of the complementary snap-fit elements 305, 306. In the embodiment as illustrated, the first snap-fit element 305 and the second snap-fit element 306 are arranged at the base element 302, in particular at the first base element part 3021.

The first snap-fit element 503 comprises an outer portion 5031 and an inner portion 5032 (see FIG. 13). Said portions 5031, 5032 deform elastically relative to each other when the snap-fit connection is established and/or undone. The same holds with respect to the second snap-fit element 504 and its portions 5042, 5041.

The handle 500 further comprises a manipulation mechanism M that allows an indirect user-operated actuation of the telescopic mechanism T. The manipulation mechanism M is operatively coupled to the telescopic mechanism T when the handle 500 is attached to the adjustment device 300 (see FIG. 14, 15). In other words, attaching the handle 500 to the adjustment device 300 also couples the manipulation mechanism M to the telescopic mechanism T. Detaching the handle 500 decouples the manipulation mechanism M.

The manipulation mechanism M comprises a manipulation gear wheel 505 and a transmission gear wheel 506. The manipulation gear wheel 505 is configured to be rotated manually and comprises external teeth 507 that interact with external teeth 508 of the transmission gear wheel 506. Both the manipulation gear wheel 505 and the transmission gear wheel 506 are rotatably mounted on the distal end 502 of the handle 500. The manipulation gear wheel 505 is rotatable around an axis that is parallel to the proximal/distal direction. The same holds with respect to the transmission gear wheel 506.

The transmission gear wheel 506 is configured for interaction with the control gear wheel 385 of the telescopic mechanism T. When the handle 500 is attached to the adjustment device 300, the external teeth 508 of the transmission gear wheel 506 are interlocked with the external teeth 386 of the control gear wheel 385. Detaching the handle 500 from the adjustment device 300 decouples the transmission gear wheel 506 from the control gear wheel 385.

The invention claimed is:

1. A tibial trial insert system, comprising:

a bearing component having a superior articulating surface for articulation with a distal femoral surface;

a plate component having an inferior fixation surface for fixation to a proximal tibia;

and an adjustment arrangement for adjusting a proximal/distal spacing between the bearing component and the plate component, wherein the adjustment arrangement comprises:

an adjustment device having a superior connector element configured to engage with an inferior surface of the bearing component, an inferior base element adapted to be placed at least indirectly upon a superior surface of the plate component, and having a telescopic mechanism operatively coupled to the connector element and to the base element, wherein the telescopic mechanism is user-operable for adjusting a thickness of the adjustment device;

and at least one shim configured for insertion between the superior surface of the plate component and an inferior surface of the base element for adjusting a height level of the adjustment device in relation to the plate component.

2. The tibial trial insert system according to claim 1, wherein the base element comprises an inferior fastening portion, and the at least one shim comprises a complementary superior fastening portion, wherein the inferior fastening portion and the superior fastening portion are configured to slidably engage in an anterior/posterior direction and to form-fittingly engage in proximal/distal direction and in medial/lateral direction.

3. The tibial trial insert system according to claim 1, wherein:

the plate component comprises a receiving recess open in a proximal direction and configured for receiving the base element, the plate component comprises an insertion aperture open in an anterior/posterior direction and leading into the receiving recess, an the insertion aperture allows the at least one shim to slide into the receiving recess in the anterior/posterior direction.

4. The tibial trial insert system according to claim 1, wherein the adjustment arrangement comprises at least one further shim configured for insertion between the superior surface of the plate component and the inferior surface of the base element and/or an inferior surface of the shim.

5. The tibial trial insert system according to claim 1, wherein the telescopic mechanism comprises at least a first translation screw and a second translation screw, the first translation screw and the second translation screw each having a screw member in thread engagement with a nut member, wherein a user-operated movement of the first translation screw and the second translation screw causes an adjustment of the thickness of the adjustment device.

6. The tibial trial insert system according to claim 5, wherein the nut member of the first translation screw and the nut member of the second translation screw each comprise external teeth, the external teeth of the nut members being at least indirectly interlocked for synchronized movement of the first translation screw and the second translation screw.

7. The tibial trial insert system according to claim 6, wherein the telescopic mechanism comprises a control gear wheel interlocked with the external teeth of the nut members such that a rotation of the control gear wheel causes synchronized rotations of the nut members.

8. The tibial trial insert system according to claim 7, wherein the telescopic mechanism comprises a third translation screw, and the control gear wheel forms a nut member of the third translation screw.

9. The tibial trial insert system according to claim 1, further comprising a handle detachably attached to the adjustment device, the handle having a manipulation mechanism operatively coupled to the telescopic mechanism and configured such that a user-operated manipulation of the manipulation mechanism causes movement of the telescopic mechanism to thereby adjust the thickness of the adjustment device.

10. The tibial trial insert system according to claim 9, wherein the handle is elongated between a proximal end and a distal end, and wherein the handle comprises at least one snap-fit element that is disposed at the distal end and configured for establishing a snap-fit connection with a complementary snap-fit element of the adjustment device.

11. The tibial trial insert system according to claim 9, wherein the manipulation mechanism comprises a manipulation gear wheel configured to be rotated manually, the manipulation gear wheel being at least indirectly interlocked with a gear wheel of the telescopic mechanism.

12. The tibial trial insert system according to claim 11, wherein the manipulation mechanism comprises at least one transmission gear wheel interlocked with the manipulation gear wheel and the gear wheel of the telescopic mechanism.

* * * * *